United States Patent
Hoffmann et al.

(10) Patent No.: US 12,090,202 B2
(45) Date of Patent: *Sep. 17, 2024

(54) COMBINATION OF PLASMA IMMUNOGLOBULIN AND ANTIGEN-SPECIFIC IMMUNOGLOBULIN FOR THE MODIFICATION OF THE IMMUNE SYSTEM AND THE TREATMENT OR PREVENTION OF ALLERGIC DISEASES

(71) Applicant: NETWORK IMMUNOLOGY INC., Vancouver (CA)

(72) Inventors: Geoffrey William Hoffmann, Vancouver (CA); Reginald M. Gorczynski, Willowdale (CA)

(73) Assignee: NETWORK IMMUNOLOGY INC., Vancouver (CA)

( * ) Notice: Subject to any disclaimer, the term of this patent is extended or adjusted under 35 U.S.C. 154(b) by 1076 days.

This patent is subject to a terminal disclaimer.

(21) Appl. No.: 16/958,609

(22) PCT Filed: Jan. 4, 2019

(86) PCT No.: PCT/CA2019/050013
§ 371 (c)(1),
(2) Date: Jun. 26, 2020

(87) PCT Pub. No.: WO2019/134047
PCT Pub. Date: Jul. 11, 2019

(65) Prior Publication Data
US 2020/0353081 A1  Nov. 12, 2020

Related U.S. Application Data

(60) Provisional application No. 62/614,131, filed on Jan. 5, 2018.

(51) Int. Cl.
| | | |
|---|---|---|
| *A61K 39/42* | (2006.01) | |
| *A61K 39/395* | (2006.01) | |
| *A61K 39/40* | (2006.01) | |
| *A61P 37/08* | (2006.01) | |

(52) U.S. Cl.
CPC ........ *A61K 39/42* (2013.01); *A61K 39/39516* (2013.01); *A61K 39/3955* (2013.01); *A61K 39/40* (2013.01); *A61P 37/08* (2018.01)

(58) Field of Classification Search
CPC .............. A61K 45/06; A61K 2039/505; A61K 2039/507; A61K 39/39516; A61K 2300/00; A61P 37/08
See application file for complete search history.

(56) References Cited

FOREIGN PATENT DOCUMENTS

| BE | 897 227 A | 1/1984 |
|---|---|---|
| BE | 897227 * | 1/1984 |
| WO | WO-2008063898 A2 * 5/2008 | ........... C07K 16/243 |
| WO | 2017/024404 A1 | 2/2017 |
| WO | 2019/134047 A1 | 7/2019 |

OTHER PUBLICATIONS

BE897227 Patent Translation (Version of the EPO, downloaded from the Web, Jul. 27, 2023) (Year: 2023).*
Gaines et al (Transfusion, 2009, vol. 49, pp. 1050-1058) (Year: 2009).*
Gorczynksi et al., "Toward a New Kind of Vaccine: A Logical Extension of the Symmetrical Immune Network Theory", Interactive Journal of Medical Research, Jul. 5, 2017, pp. 1-17, vol. 6, No. 2, Interact J Med Res.
Gorczyinski et al., "Towards a new kind of vaccine", bioRxiv, Jan. 18, 2017, Cold Spring Harbor Laboratory, https://doi.org/10.1101/101345.
Nahm et al., "Effects of Intramuscular Injection of Autologous Immunoglobulin on Clinical Severity and Serum IgE Concentration in Patients with Atopic Dermatitis", Dermatology, Jun. 20, 2015, pp. 145-151, vol. 231, S. Karger AG, Basel.
Rabinovitch et al., "The role of immunoglobulin therapy in allergic diseases", Allergy, 1999, pp. 662-668, vol. 54, Munksgaard.
Supplementary European Search Report received for Application No. 20831330.1, completed Jun. 21, 2023.
Ahmed, A.R., et al., "Concensus Statement on the Use of Intraveneous Immunoglobulin Therapy in the Treatment of Autoimmune Mucocutaneous, Blistering Diseases" Arch Dermatol, vol. 139, Aug. 2003, pp. 1051-1059.
Gorczynski, R.M., et al., "Combined IMIG and immune Ig attenuates inflammatory colitis in mice," International immunopharmacology 83, 2020, 8 pages.
Nobre, F., et al., "Antibody levels to tetanus, diphtheria, measles and varicella in patients with primary immunodeficency undergoing intravenous immunoglobulin therapy: a prospective study," BMC Immunology 15 (26), 2014, 7 pages.
Notice of Reasons of Refusal received for Japanese Application No. 2020-557367, dated Oct. 25, 2022.
European Search Report for Application No. 19736264.3, dated Oct. 14, 2021.
Cattepoel, S., et al., "Effect of IVIG Formulation on IgG Binding to Self- and Exo-Antigens In Vitro and In Vivo," PLOS ONE, vol. 11, No. 8, Aug. 25, 2016, 14 pages.
Cho, S., et al., "Immunomodulatory effects induced by intramuscular administration of autologous total immunoglobulin G in patients with atopic dermatitis," International Immunopharmacology, vol. 52, Aug. 31, 2017, pp. 1-6.

(Continued)

*Primary Examiner* — Karen A. Canella
(74) *Attorney, Agent, or Firm* — Greer, Burns & Crain, Ltd

(57) ABSTRACT

A method of use of plasma immunoglobulin, such as intramuscular immunoglobulin, in combination with polyclonal antigen-specific immunoglobulin in the treatment or prevention of allergic disease is provided. Also provided is a pharmaceutical composition including plasma immunoglobulin in combination with polyclonal antigen-specific immunoglobulin.

18 Claims, 8 Drawing Sheets

(56) References Cited

OTHER PUBLICATIONS

Fernanda, A., et al., "Antibody levels to tetanus, diphtheria, measles and varicella in patients with primary immunodeficiency undergoing intravenous immunoglobulin therapy: a prospective study," BMC Immunology, vol. 15, No. 26, Jun. 21, 2014. pp. 1-7.

Kaufman, G., et al., "Intravenous immunoglobulin attenuates airway hyperresponsiveness in a murine model of allergic asthma," Intravenous immunoglobulin attenuates AHR, Clinical & Experimental Allergy, vol. 41, No. 5, May 1, 2011, pp. 718-728.

* cited by examiner

COMBINATION OF PLASMA IMMUNOGLOBULIN AND ANTIGEN-SPECIFIC IMMUNOGLOBULIN FOR THE MODIFICATION OF THE IMMUNE SYSTEM AND THE TREATMENT OR PREVENTION OF ALLERGIC DISEASES

BACKGROUND

This invention relates to the treatment of allergic disease. In particular, this invention relates to the use of pooled immunoglobulin in combination with antigen-specific polyclonal immunoglobulin in the prevention or treatment of allergic diseases.

Allergic diseases afflict a significant fraction of the human population and of the population of pets. Allergen immunotherapy can sometimes be used to build up an individual's tolerance to allergens. In the therapy, allergen injections are given in two phases: a build-up phase and a maintenance phase. The build-up phase can involve injections with increasing amounts of allergens about one to three times per week for three to six months. Once an effective dose is reached, the maintenance phase begins with further injections about once every two to four weeks for several years. Both the build-up phase and maintenance phase are therefore quite onerous.

It is an object of this invention to provide improved pharmaceutical compositions and methods for the treatment or prevention of allergic diseases.

This and other objects of the invention will be better understood by reference to the detailed description of the preferred embodiment which follows. Note that the object referred to above is a statement of what motivated the invention rather than promises. Not all the objects are necessarily met by all embodiments of the invention described below or by the invention defined by each of the claims.

SUMMARY

According to one aspect of the invention, a combination of plasma immunoglobulin and antigen-specific immunoglobulin may be used for the treatment or prevention of allergic disease.

In another aspect, the invention comprises the use of a combination of plasma immunoglobulin and antigen-specific immunoglobulin for the treatment or prevention of allergic disease.

In another aspect, the invention is a pharmaceutical composition for the treatment or prevention of allergic disease. The pharmaceutical composition comprises plasma immunoglobulin and antigen-specific immunoglobulin.

In a further aspect, the plasma immunoglobulin is intramuscular immunoglobulin.

In a further aspect, the intramuscular immunoglobulin is human intramuscular immunoglobulin.

In a further aspect, the plasma immunoglobulin is human plasma immunoglobulin.

In a further aspect, the plasma immunoglobulin is from a non-human species.

In a further aspect, the plasma immunoglobulin and the antigen-specific immunoglobulin are from the same species.

In another aspect, the antigen-specific immunoglobulin is selected from the group consisting of polyclonal anti-Tetanus toxoid immunoglobulin, polyclonal anti-Rh immunoglobulin, polyclonal anti-hepatitis B immunoglobulin, polyclonal anti-rabies immunoglobulin, and polyclonal anti-varicella immunoglobulin.

In another aspect, the plasma immunoglobulin is greater than 50 mg per kg body weight.

In a further aspect, the invention is a method of treating or preventing allergic disease comprising administering injections of plasma immunoglobulin and antigen-specific immunoglobulin.

In a further aspect, the invention is a kit comprising aliquots of plasma immunoglobulin, aliquots of antigen-specific immunoglobulin, and instructions associated with the kit directing use of the aliquots of plasma immunoglobulin and the aliquots of antigen-specific immunoglobulin for the treatment or prevention of allergic disease.

In a further aspect, the invention is a kit comprising aliquots of mixtures of plasma immunoglobulin and antigen-specific immunoglobulin, and instructions associated with the kit directing use of the aliquots of mixtures of plasma immunoglobulin and antigen-specific immunoglobulin for the treatment or prevention of allergic disease.

The foregoing may cover only some of the aspects of the invention. Other aspects of the invention may be appreciated by reference to the following description of at least one preferred mode for carrying out the invention in terms of one or more examples. The following mode(s) for carrying out the invention is not a definition of the invention itself, but is only an example that embodies the inventive features of the invention.

BRIEF DESCRIPTION OF THE DRAWINGS

At least one mode of carrying out the invention in terms of several examples will be described by reference to the drawings below in which.

DETAILED DESCRIPTION

Figure 1A:
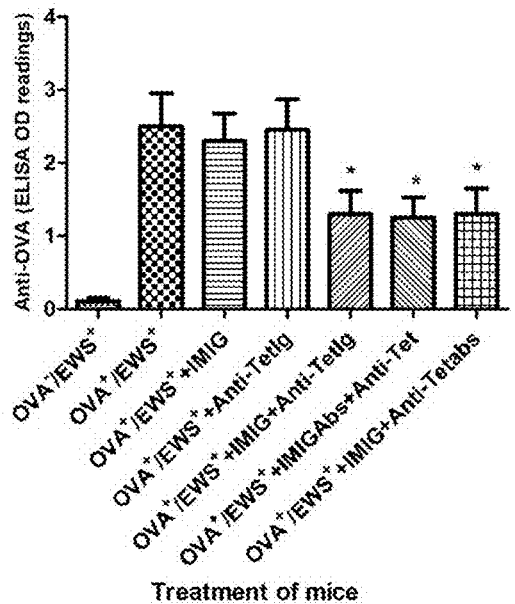
FIG. 1A is a graph showing the attenuation of an anti-OVA IgE response by combined injections of IMIG and polyclonal anti-Tetanus toxoid Ig.

The pharmaceutical compositions of the present invention are a combination of pooled plasma immunoglobulin and antigen-specific polyclonal immunoglobulin.

Plasma immunoglobulin is typically prepared from the serum of at least 1000 donors and has been used to treat patients with primary immunodeficiency diseases. Depending on how the plasma immunoglobulin is formulated and administered, it may be referred to as intramuscular immunoglobulin ("IMIG"), intravenous immunoglobulin ("IVIG"), subcutaneous immunoglobulin ("SCIG"), or intraperitoneal immunoglobulin ("IPIG").

Antigen-specific polyclonal immunoglobulin is immunoglobulin prepared with a high antibody count against a specific pathogen, such as Varicella-zoster virus, or against a specific antigen, such as Tetanus toxoid.

The inventors have found that the combination of pooled plasma immunoglobulin and antigen-specific polyclonal immunoglobulin is useful for the treatment or prevention of allergic diseases.

As will be described in detail below, the inventors conducted experiments using various antigen-specific immunoglobulins against various antigens. In view of the significant differences in preparation and chemical composition between the antigen-specific immunoglobulins used (polyclonal anti-Tetanus immunoglobulin, polyclonal anti-Rabies immunoglobulin, and polyclonal anti-Varicella immunoglobulin), the combination of plasma immunoglobulin with any antigen-specific immunoglobulin (including but not limited to polyclonal anti-Rh immunoglobulin and polyclonal anti-hepatitis B immunoglobulin) is predicted to result in a similar modification of the immune system of the treated human or animal and to similarly prevent and/or treat allergic diseases.

For the treatment and prevention of allergic diseases in humans and pets, the plasma immunoglobulin component of the combination may be plasma immunoglobulin approved for use in humans such as, but not limited to, Gamunex™ and Hizentra™.

The plasma immunoglobulin and antigen-specific polyclonal immunoglobulin may be administered in any suitable manner. For example, the antibodies may be administered in a non-immunogenic form, that is without an adjuvant, in a non-immunogenic amount, for example intramuscularly, intravenously, subcutaneously, or intraperitoneally. A pharmaceutical composition comprising the combination of plasma immunoglobulin and antigen-specific polyclonal immunoglobulin may include a pharmaceutically acceptable carrier, such as buffered saline, phosphate buffered saline, or phosphate buffered saline at neutral pH.

Another aspect of the invention is a kit comprising aliquots of plasma immunoglobulin, aliquots of polyclonal antigen-specific immunoglobulin, and instructions directing use of such two different aliquots for the treatment or prevention of allergic disease.

Another aspect of the invention is a kit comprising aliquots of a mixture of plasma immunoglobulin and polyclonal antigen-specific immunoglobulin and instructions directing use of such aliquots for the treatment or prevention of allergic disease.

The antibodies may be administered at any suitable site and time. However, the antibodies are preferably administered contemporaneously or substantially contemporaneously. The antibodies may be administered in separate compositions sequentially or contemporaneously or together as a mixture.

Example 1

Allergy Experiment Protocol with Polyclonal Human IMIG and Polyclonal Human Anti-Tetanus Ig Five BALB/c mice (8 weeks of age at initiation of study) were used per group. All mice except a control group (Group 1—see below) received ovalbumin (10 μg OVA plus Al(OH)$_3$) intraperitoneally in 0.3 ml phosphate buffered saline ("PBS") on day 0 and day 14 with a further boost on day 56. All mice received egg white solution (filtered 20% (w/v) EWS) in their drinking water from day 14.

Mice receiving intramuscular immunoglobulin (Gamunex™ 25 µg: Grifols) were given intramuscular injections in 0.05 ml PBS in the left gluteus muscle at days -2, 7, 14, 21, 28, 35, and 42. Animals receiving Anti-Tetanus immune Ig (HyperTET™ 25 µg: Grifols) were given intramuscular injections in 0.05 ml PBS in the right deltoid muscle at days -2, 7, 14, 21, 28, 35, and 42. In some cases IMIG or Anti-Tetanus was absorbed with Tetanus toxoid (×3) before use. The control groups received PBS only in the same sites.

The following groups were used.
Group 1: OVA$^-$/EWS$^+$
Group 2: OVA$^-$/EWS$^+$
Group 3: As for group 2+IMIG
Group 4: As for group 2+Anti-Tet Ig
Group 5: As for group 2+IMIG+anti-Tet Ig
Group 6: As for group 2+IMIG (absorbed×3 with Tet)+ ant-Tet Ig
Group 7: As for group 2+IMIG+anti-Tet Ig (absorbed with Tet×3)

All mice were sacrificed at day 63 of the study. On sacrifice, serum IgE to OVA obtained by cardiac puncture was measured by ELISA using plates coated with 100 ng/well of OVA and developed with HRP-anti-mouse IgE and appropriate substrate.

In addition, $5 \times 10^6$ splenocytes from individual animals were challenged in vitro in 2 ml medium with 1 µg/ml OVA for 72 hr and IL-2/IL-4 measured in culture supernatants using commercial ELISA Kits (eBIOSciences).

Results

Figure 1B:
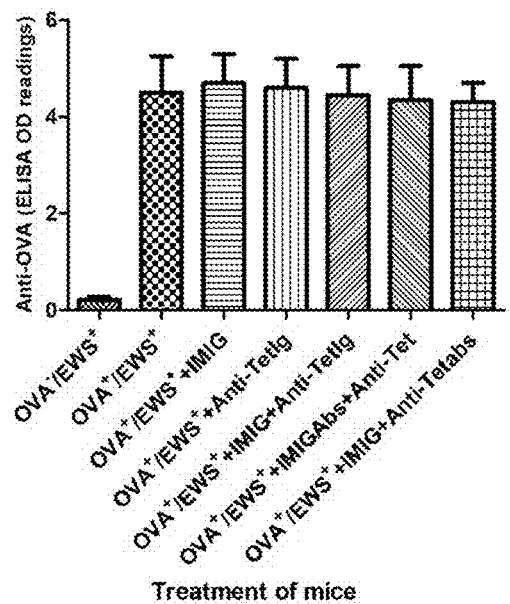
FIG. 1B is a graph showing no change in an anti-OVA IgG response by combined injections of IMIG and polyclonal anti-Tetanus toxoid Ig.

FIG. 1A shows that a combination of IMIG and polyclonal anti-Tetanus Ig results in significant suppression of OVA-specific IgE and FIG. 1B shows no significant effect on OVA-specific IgG. Referring now to FIG. 1A, absorption of IMIG or polyclonal anti-Tetanus with Tetanus (groups 6 and 7) made no difference. This suggests that the active pharmaceutical ingredient is not the anti-Tetanus antibodies.

Figure 1C:
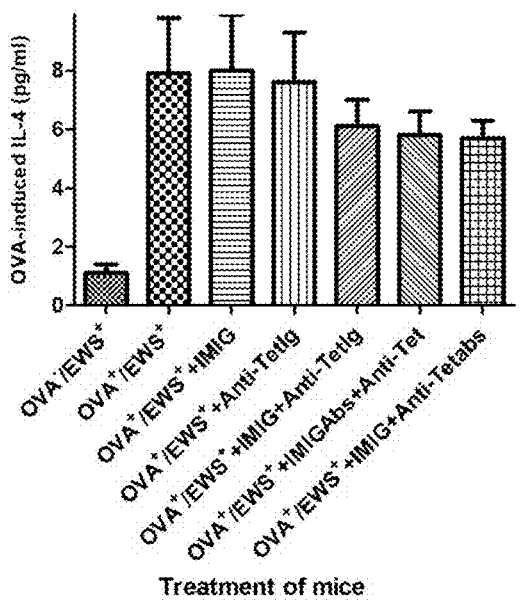
FIG. 1C is a graph showing OVA-induced IL-4 in splenocytes of OVA immunized mice receiving combined injections of IMIG and polyclonal anti-Tet Ig.
Figure 1D:
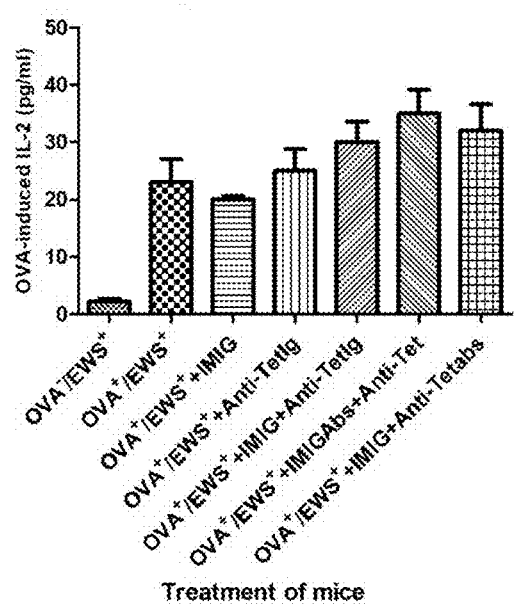
FIG. 1D is a graph showing OVA-induced IL-2 in splenocytes of OVA immunized mice receiving combined injections of IMIG and polyclonal anti-Tet Ig.

FIG. 1C shows a decrease in the levels of OVA-induced IL-4 in the splenocytes of mice in groups 5, 6, and 7 that received combined injections of IMIG and anti-Tetanus Ig. When considered together with FIG. 1D showing OVA-induced IL-2 levels, it is apparent that the ratio of IL-4 to IL-2 is smaller for the groups treated with IMIG plus anti-Tetanus Ig (groups 5, 6, and 7) than the control groups 2, 3 and 4. This result is consistent with suppression of allergy and the results shown in FIGS. 1A and 1B.

Example 2

Allergy Experiment Protocol with Polyclonal Human IMIG and Polyclonal Human Anti-Varicella Ig Eight BALB/c mice (8 weeks of age at initiation of study) were used per group. All mice except a control group (Group 1—see below) received ovalbumin (10 µg OVA plus Al(OH)$_3$) intraperitoneally in 0.3 ml PBS on day 0, day 14, and day 42. All mice received egg white solution (filtered 20% (w/v) EWS) in their drinking water from days 14-42.

IMIG (Gamunex™ 25 µg: Grifols) and anti-Varicella Ig (25 µg: Grifols) was infused weekly intravenously from days 7-35.

The following groups were used.
Group 1: OVA$^-$/EWS$^+$
Group 2: OVA$^-$/EWS$^+$
Group 3: As for group 2+IMIG
Group 4: As for group 2+Anti-Varicella Ig
Group 5: As for group 2+IMIG+anti-Varicella Ig All mice were sacrificed at day 49 of the study. On sacrifice, serum IgE to OVA obtained by cardiac puncture was measured by ELISA using plates coated with 100 ng/well of OVA and developed with HRP-anti-mouse IgE and appropriate substrate.

In addition, $5 \times 10^6$ splenocytes from individual animals were challenged in vitro in 2 ml medium with 1 µg/ml OVA for 72 hr and IL-2/IL-4 measured in culture supernatants using commercial ELISA Kits (eBIOSciences).

Results

Figure 2A:
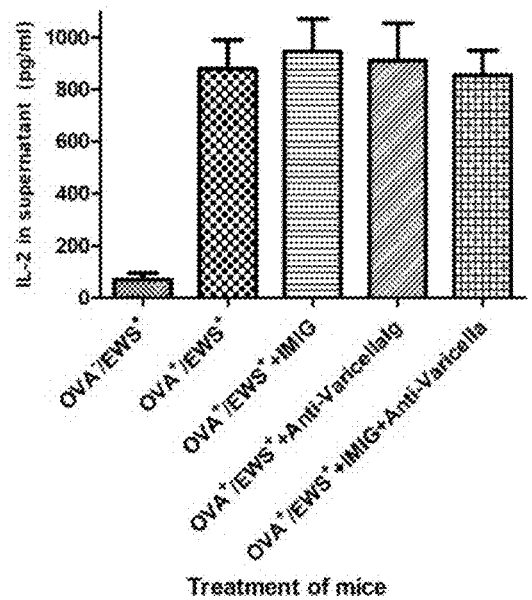
FIG. 2A is a graph showing OVA-induced IL-2 in splenocytes of OVA immunized mice injected with IMIG and anti-Varicella Ig.
Figure 2B:
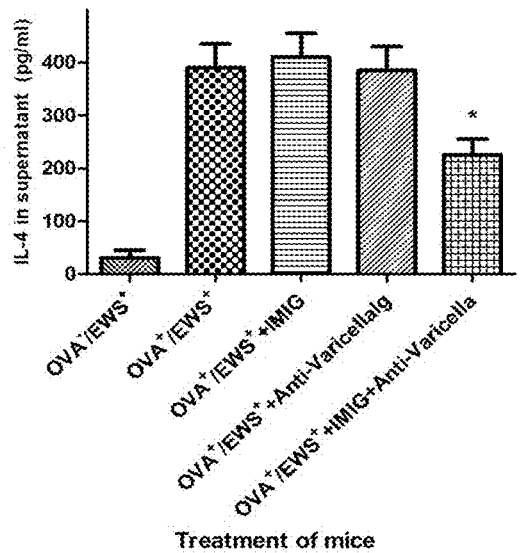
FIG. 2B is a graph showing OVA-induced IL-4 in splenocytes of OVA immunized mice injected with IMIG and anti-Varicella Ig.

FIG. 2A shows that there was no attenuation of IL-2 production from the OVA-stimulated individual splenocytes of mice. In contrast, FIG. 2B shows a clear attenuation of IL-4 production. These results are consistent with the study done in EXAMPLE 1 using combined injection of IMIG and anti-Tetanus Ig (see FIGS. 1C and 1D).

Example 3

Allergy Experiment Protocol with Polyclonal Human IMIG and Polyclonal Human Anti-Tetanus Ig, or Polyclonal Dog Ig and Dog Anti-Rabies Ig, Using Beagle Dogs Sensitized to Peanut Butter In a modification of the protocol in EXAMPLE 1 and EXAMPLE 2, the inventors considered whether they could attenuate allergic sensitization in large animals (Beagle dogs) where previous literature reports indicate a high prevalence (>80%) of induced allergic sensitization to peanut butter applied topically.

Animals received weekly topical exposure to peanut butter (abdomen) with the first exposure occurring 1 week before treatment. The next 5 exposures of peanut better were with 5 weekly treatments with combined dog Igs (IMIG and pooled dog anti-Rabies immune Ig) or with combined human Igs (IMIG and Anti-Tet Ig). After 5 weekly treatments all animals received a further 3 treatments given at 14 d intervals of the same Ig mixes. Finally, all dogs received an oral challenge with peanut butter, and serum IgG, serum IgE, and peanut butter induced IL-2/IL-4 production was measured.

Dogs receiving dog intramuscular immunoglobulin (Innovative Research, USA) were given 1 mg/kg intramuscular injections in 0.5 ml PBS in the gluteus muscle and dogs receiving pooled dog anti-Rabies immune Ig (prepared from pooled dogs re-immunized with rabies vaccine) were given 1 mg/kg intramuscular injections in 0.5 ml PBS in the opposite gluteus muscle.

Dogs receiving human intramuscular immunoglobulin (Gamunex™: Grifols) were given 1 mg/kg intramuscular injections in 0.5 ml PBS in the gluteus muscle and dogs receiving human Anti-Tetanus Ig (HyperTET™: Grifols) were given 1 mg/kg intramuscular injections in 0.5 ml PBS in the opposite gluteus muscle.

Results

Figure 3A:
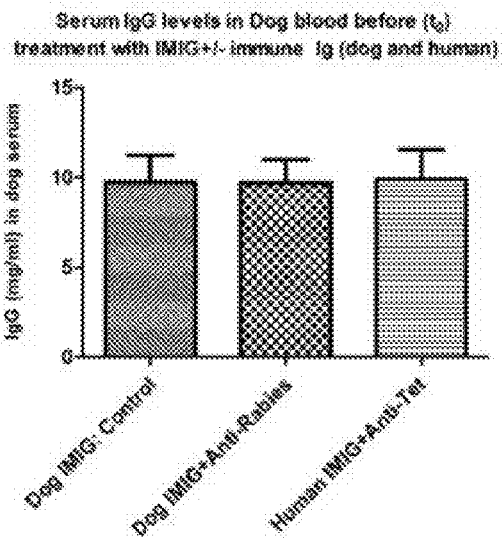
FIG. 3A is a graph showing the total serum IgG levels in dog blood before sensitization with peanut butter and treatment with dog IMIG and dog anti-Rabies immune Ig or treatment with human IMIG and human anti-Tetanus Ig.
Figure 3B:
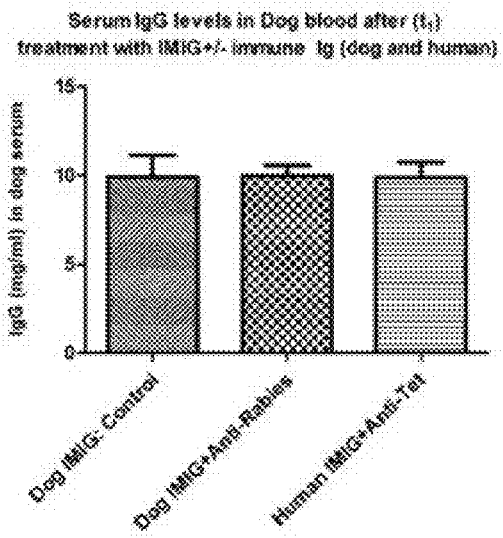
FIG. 3B is a graph showing the total serum IgG levels in dog blood after sensitization with peanut butter and treatment with dog IMIG and dog anti-Rabies immune Ig or treatment with human IMIG and human anti-Tetanus Ig.
Figure 3C:
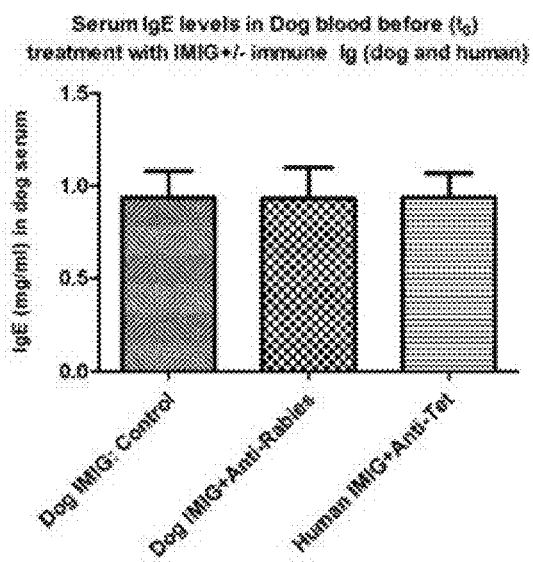
FIG. 3C is a graph showing the total serum IgE levels in dog blood before sensitization with peanut butter and treatment with dog IMIG and dog anti-Rabies immune Ig or treatment with human IMIG and human anti-Tetanus Ig.
Figure 3D:
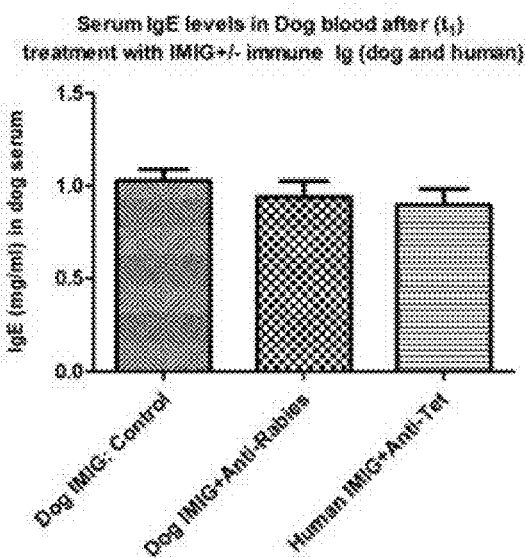
FIG. 3D is a graph showing the total serum IgE levels in dog blood after sensitization with peanut butter and treatment with dog IMIG and dog anti-Rabies immune Ig or treatment with human IMIG and human anti-Tetanus Ig.

FIGS. 3A and 3B show a comparison of the total serum IgG levels at the start (t0) and end (t1) of the study respectively. FIGS. 3C and 3D show a comparison of the total serum IgE levels at the start (t0) and end (t1) of the study respectively. While there were no significant changes in the IgG levels, a reduction in the IgE levels was observed both for the treatment with dog IMIG and dog anti-Rabies Ig and for the treatment with human IMIG and human anti-Tetanus Ig.

Figure 3E:
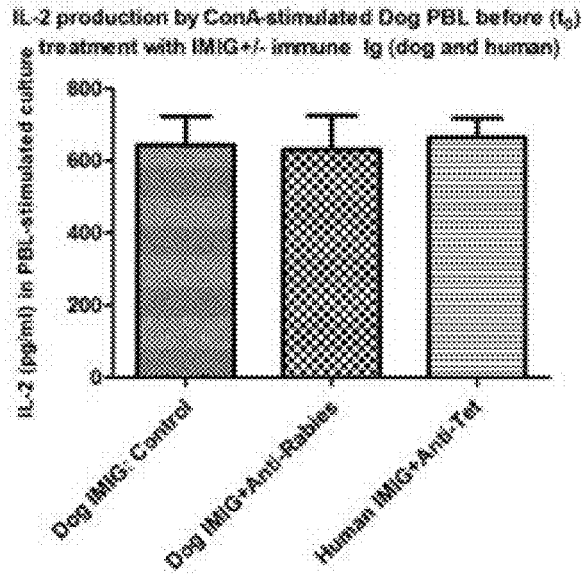
FIG. 3E is a graph showing IL-2 production by ConA-stimulated peripheral blood lymphocytes of dogs before sensitization with peanut butter and treatment with dog IMIG and dog anti-Rabies immune Ig or treatment with human IMIG and human anti-Tetanus Ig.
Figure 3F:
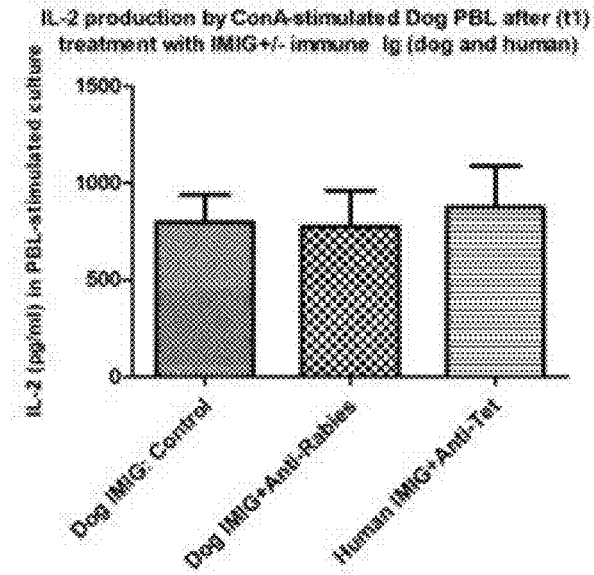
FIG. 3F is a graph showing IL-2 production by ConA-stimulated peripheral blood lymphocytes of dogs after sensitization with peanut butter and treatment with dog IMIG and dog anti-Rabies immune Ig or treatment with human IMIG and human anti-Tetanus Ig.

FIGS. 3E and 3F show a comparison of the IL-2 production by conconavalin A (ConA) in dog peripheral blood lymphocytes (PBL) before (t0) and after (t1) treatment respectively.

Figure 3G:
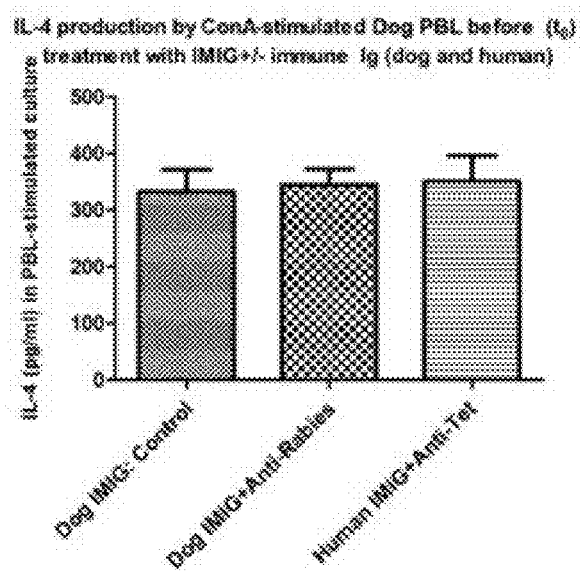
FIG. 3G is a graph showing IL-4 production by ConA-stimulated peripheral blood lymphocytes of dogs before sensitization with peanut butter and treatment with dog IMIG and dog anti-Rabies immune Ig or treatment with human IMIG and human anti-Tetanus Ig.
Figure 3H:
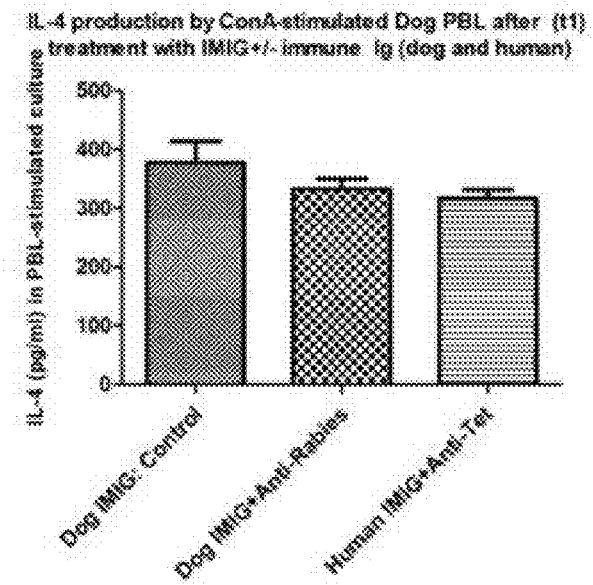
FIG. 3H is a graph showing IL-4 production by ConA-stimulated peripheral blood lymphocytes of dogs after sensitization with peanut butter and treatment with dog IMIG and dog anti-Rabies immune Ig or treatment with human IMIG and human anti-Tetanus Ig.

FIGS. 3G and 3H shows a comparison of the IL-4 production by Con-A in dog PBL before (t0) and after (t1) treatment respectively.

Figure 3I:
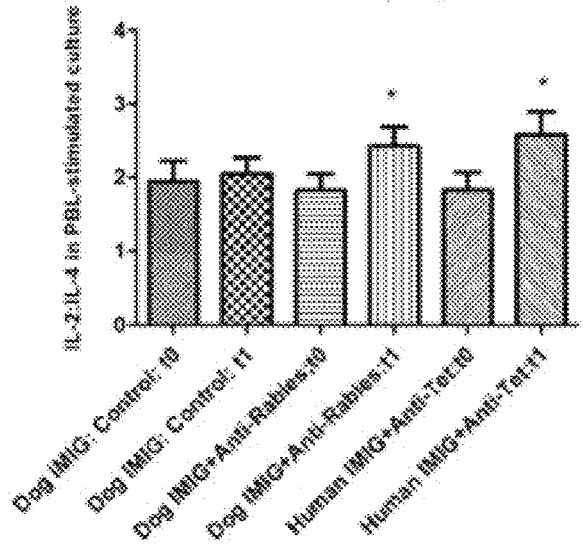
FIG. 3I is a graph showing the ratio of IL-2/IL-4 production levels by ConA-stimulated peripheral blood lymphocytes of dogs before and after sensitization with peanut butter and treatment with dog IMIG and dog anti-Rabies immune Ig or treatment with human IMIG and human anti-Tetanus Ig.

FIG. 3I shows a comparison of the IL-2/IL-4 induction by ConA in dog PBL before/after Ig treatment. Note that even for this polyclonal response, the IL-2/IL-4 ratio is enhanced in dogs after treatment with either dog IgGs or human IgGs (*, $p<0.05$).

Figure 3J:
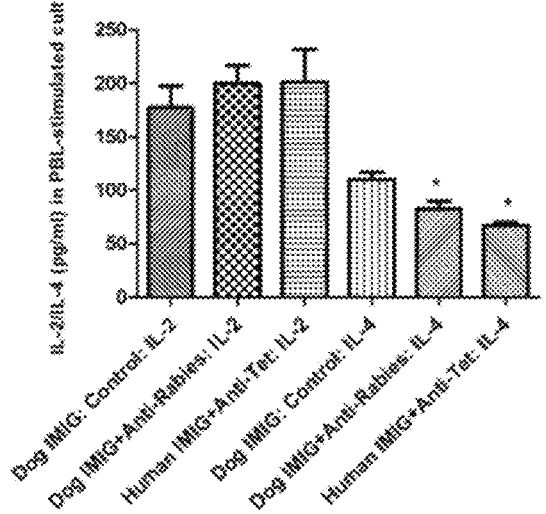
FIG. 3J is a graph showing the IL-2 and IL-4 production by peanut butter Ag-stimulated peripheral blood lymphocytes of dogs after sensitization with peanut butter and treatment with dog IMIG and dog anti-Rabies immune Ig or treatment with human IMIG and human anti-Tetanus Ig.
Figure 3K:
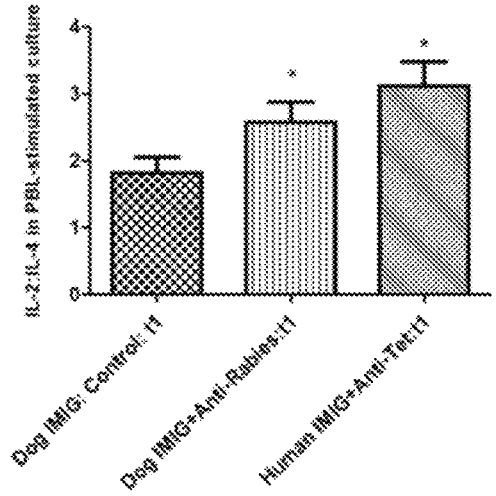
FIG. 3K is a graph showing the ratio of IL-2/IL-4 production levels by peanut butter Ag-stimulated peripheral blood lymphocytes of dogs after sensitization with peanut butter and treatment with dog IMIG and dog anti-Rabies immune Ig or treatment with human IMIG and human anti-Tetanus Ig.

FIG. 3J shows that IL-2 and IL-4 productions by peanut butter stimulated dog PBL after treatment with dog IMIG and dog anti-Rabies Ig and after treatment with human IMIG and human anti-Tetanus Ig. FIG. 3K shows the IL-2:IL-4 ratios after treatment. Consistent with the other experiments, IL-4 production was attenuated by Ig treatment, but IL-2 production was not. Additionally, the IL-2:IL-4 ratios were elevated after treatment (*, $p<0.05$).

Example 4

Dose Response Study—Polyclonal Human IMIG and Polyclonal Human Anti-Tetanus Ig in Pre-Immune Mice The inventors also conducted a dose response study using polyclonal human IMIG and polyclonal human anti-Tetanus Ig in pre-immune mice.

In the dose response study, all groups had five BALB/c mice each. Mice were approximately 25 grams. All mice received OVA (10 µg OVA plus $Al(OH)_3$) on day 0 and day 14 with a boost on day 56. All mice received EWS (filtered 20% (w/v) egg white solution in their drinking bottle) from day 14.

Mice began treatment with immunoglobulin injections on days 56, 63, 70, 77, and 84.

The following groups were used:
Group 1 (control): OVA immunization and EWS
Group 2: As for Group 1+IMIG (250 µg/mouse)+anti-Tet Ig (10 µg/mouse)
Group 3: As for Group 1+IMIG (250 µg/mouse)+anti-Tet Ig (50 µg/mouse)
Group 4: As for Group 1+IMIG (250 µg/mouse)+anti-Tet Ig (250 µg/mouse)
Group 5: As for Group 1+IMIG (50 µg/mouse)+anti-Tet Ig (10 µg/mouse)
Group 6: As for Group 1+IMIG (50 µg/mouse)+anti-Tet Ig (50 µg/mouse)
Group 7: As for Group 1+IMIG (50 µg/mouse)+anti-Tet Ig (250 µg/mouse)
Group 8: As for Group 1+IMIG (10 µg/mouse)+anti-Tet Ig (10 µg/mouse)
Group 9: As for Group 1+IMIG (10 µg/mouse)+anti-Tet Ig (50 µg/mouse)
Group 10: As for Group 1+IMIG (10 µg/mouse)+anti-Tet Ig (250 µg/mouse)
Group 11: As for Group 1+IMIG (50 µg/mouse)+anti-Tet Ig (50 µg/mouse)+CoQ10 ip (100 µg/mouse) q2d from days 56-90
Group 12: As for Group 1+IMIG (250 µg/mouse)
Group 13: As for Group 1+Anti-Tet Ig (50 µg/mouse)

A final boost with OVA was on day 90 and the mice were sacrificed on day 97.

Serum OVA-specific IgG/IgE was measured by ELISA. Additionally, $2 \times 10^6$ splenocytes were challenged in vitro in 2 ml medium with 1 µg/ml OVA for 72 hr and IL-2/IL-4 was measured in culture supernatants using commercial ELISA Kits (BioLegend).

Results

Figure 4A:
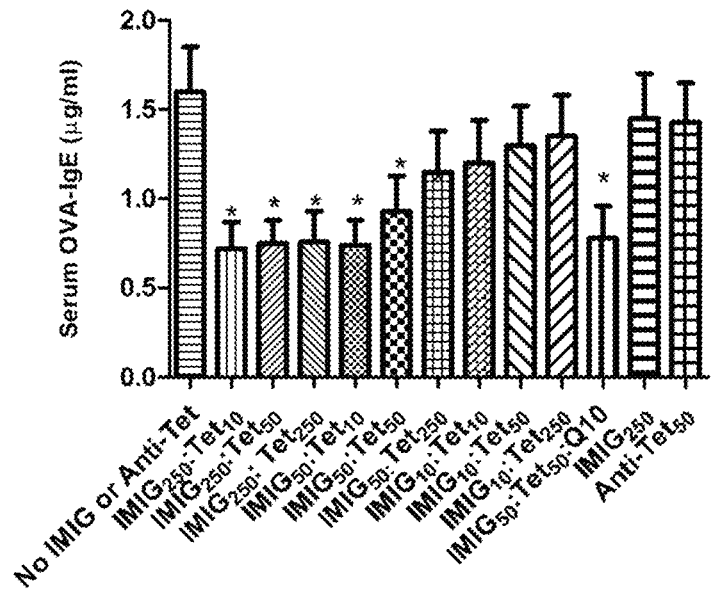
FIG. 4A is a graph showing OVA-specific IgE serum levels in OVA immunized mice after combined infusion of varying doses of IMIG and anti-Tetanus Ig.
Figure 4B:
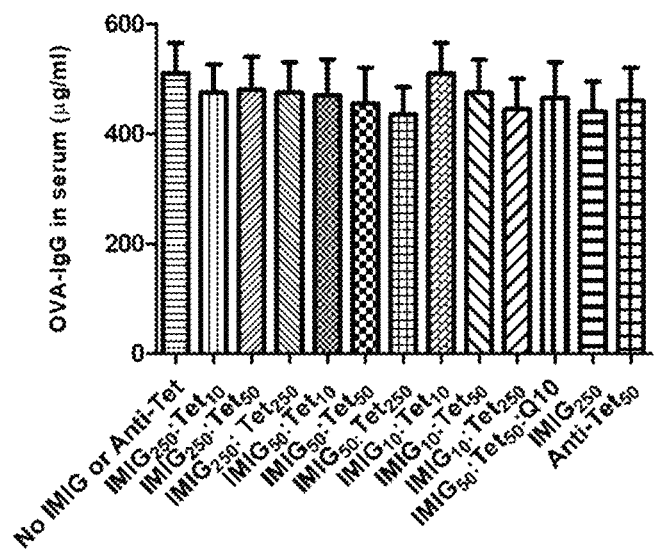
FIG. 4B is a graph showing OVA-specific IgG serum levels in OVA immunized mice after combined infusion of varying doses of IMIG and anti-Tetanus Ig.

FIGS. 4A and 4B show that optimal suppression of IgE responses occurred with IMIG doses of 250 and 50 µg/mouse and across a broad spectrum of anti-Tet dosing (from 10-2504/mouse). At lower IMIG doses (10 µg/mouse) suppression was less evident. There was some synergy in suppression at lower doses of IMIG (50) and anti-Tet (50) if animals also received CoQ10 as anti-oxidant every 2 d (1004/mouse). No attenuation of IgG responses occurred (FIG. 4B).

Figure 4C:
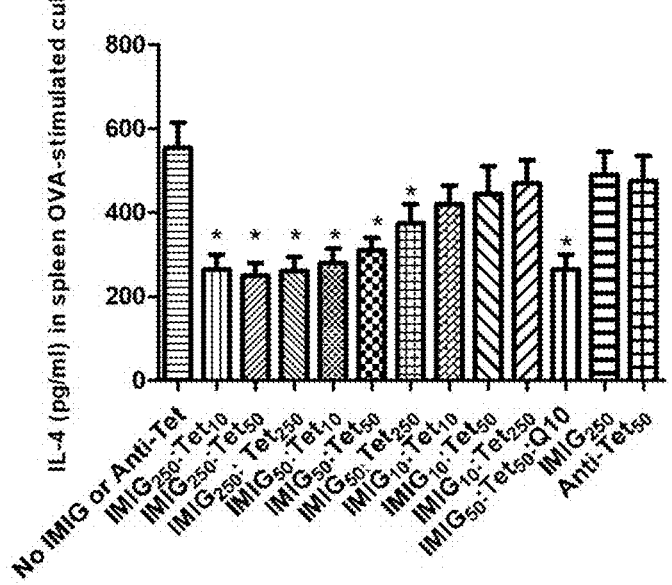
FIG. 4C is a graph showing IL-4 production by OVA-stimulated splenocytes in OVA immunized mice after combined infusion of varying doses of IMIG and anti-Tetanus Ig.
Figure 4D:
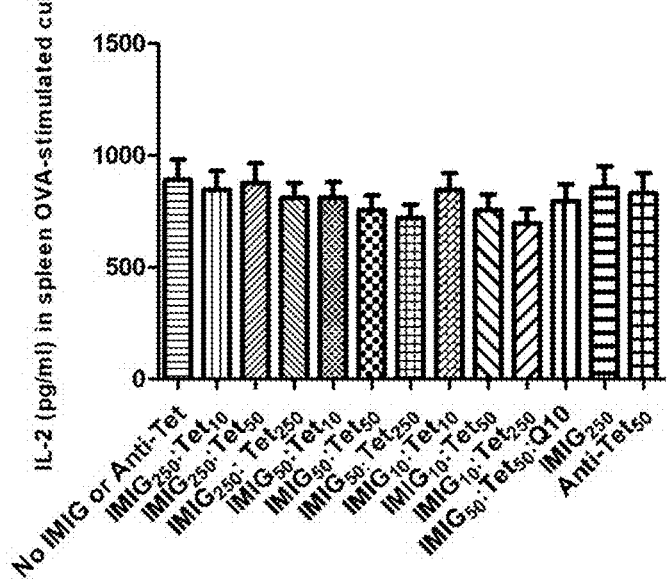
FIG. 4D is a graph showing IL-2 production by OVA-stimulated splenocytes in OVA immunized mice after combined infusion of varying doses of IMIG and anti-Tetanus Ig.
Figure 4E:
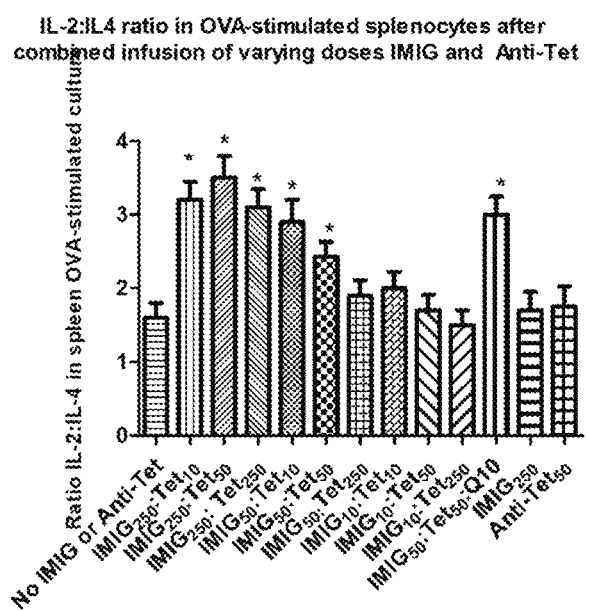
FIG. 4E is a graph showing the ratio of IL-2/IL-4 production levels by OVA-stimulated splenocytes of OVA immunized mice after combined infusion of varying doses of IMIG and anti-Tetanus Ig.

FIGS. 4C, 4D, and 4E confirm the data of FIGS. 4A and 4B using IL-4 and IL-2 production as readout. Again suppression of IL-4 but not IL-2 production was seen with IMIG doses of 250 and 50 µg/mouse and across a broad spectrum of anti-Tet dosing (from 10-2504/mouse). At lower IMIG doses ($10_4$/mouse) suppression was less evident. There was synergy in suppression at lower doses of IMIG (50) and anti-Tet (50) if animals also received CoQ10 as anti-oxidant every 2 d (1004/mouse). These data are further emphasized by comparison of IL-2:IL-4 ratios as shown in FIG. 4E.

In the foregoing description, exemplary modes for carrying out the invention in terms of examples have been described. However, the scope of the claims should not be limited by those examples, but should be given the broadest interpretation consistent with the description as a whole. The specification and drawings are, accordingly, to be regarded in an illustrative rather than a restrictive sense.

The invention claimed is:

1. A pharmaceutical composition for the treatment or prevention of allergic disease in a mammalian subject, said pharmaceutical composition comprising a combination of:
   (a) pooled plasma immunoglobulin; and
   (b) additional antigen specific immunoglobulin, wherein said antigen-specific immunoglobulin is selected from the group consisting of polyclonal anti-tetanus toxoid immunoglobulin, polyclonal anti-hepatitis B immunoglobulin, polyclonal anti-rabies immunoglobulin, and polyclonal anti-varicella immunoglobulin.

2. The pharmaceutical composition of claim 1 wherein said plasma immunoglobulin is intramuscular immunoglobulin.

3. The pharmaceutical composition of claim 2 wherein said intramuscular immunoglobulin is human intramuscular immunoglobulin.

4. The pharmaceutical composition of claim 1 wherein said plasma immunoglobulin is human plasma immunoglobulin.

5. The pharmaceutical composition of claim 1 wherein said plasma immunoglobulin is from a non-human species.

6. The pharmaceutical composition of claim 1 wherein said plasma immunoglobulin and said additional antigen-specific immunoglobulin are from the same species.

7. A method of treating or preventing an allergic disease, comprising administering to a mammalian subject in need thereof a combination of
   (a) pooled plasma immunoglobulin; and
   (b) additional antigen-specific immunoglobulin.

8. The method of claim 7, wherein said additional antigen-specific immunoglobulin is selected from the group consisting of polyclonal anti-tetanus toxoid immunoglobulin, polyclonal anti-Rh immunoglobulin, polyclonal anti-hepatitis B immunoglobulin, polyclonal anti-rabies immunoglobulin, and polyclonal anti-varicella immunoglobulin.

9. The method of claim 7, wherein the allergic disease is selected from ovalbumin allergy and peanut allergy.

10. The method of claim 9, wherein said additional antigen-specific immunoglobulin is selected from the group consisting of polyclonal anti-tetanus toxoid immunoglobulin, polyclonal anti-Rh immunoglobulin, polyclonal anti-hepatitis B immunoglobulin, polyclonal anti-rabies immunoglobulin, and polyclonal anti-varicella immunoglobulin.

11. The method of claim 7, wherein administering to a mammalian subject in need thereof a combination of pooled plasma immunoglobulin and additional antigen-specific immunoglobulin, is by injection.

12. The method of claim 11, wherein the injection is intramuscular injection.

13. The method of claim 7, wherein said pooled plasma immunoglobulin is administered to said mammalian subject at a dose of about 2 to 10 mg/kg body weight and said additional antigen-specific immunoglobulin is administered to said subject at a dose of about 0.4 to 10 mg/kg body weight every week.

14. A method of treating or preventing an ovalbumin allergy or peanut allergy, comprising administering to a mammalian subject in need thereof a pharmaceutical composition comprising a combination of pooled plasma immunoglobulin and antigen-specific immunoglobulin.

15. The method of claim 14, wherein said antigen-specific immunoglobulin is selected from the group consisting of polyclonal anti-tetanus toxoid immunoglobulin, polyclonal anti-Rh immunoglobulin, polyclonal anti-hepatitis B immunoglobulin, polyclonal anti-rabies immunoglobulin, and polyclonal anti-varicella immunoglobulin.

16. The method of claim 14, wherein administering to a mammalian subject in need thereof a combination of pooled plasma immunoglobulin and antigen-specific immunoglobulin, is by injection.

17. The method of claim 16, wherein the injection is intramuscular injection.

18. The method of claim 14, wherein said pooled plasma immunoglobulin is administered to said mammalian subject at a dose of about 2 to 10 mg/kg body weight and said antigen-specific immunoglobulin is administered to said subject at a dose of about 0.4 to 10 mg/kg body weight every week.

* * * * *